Figure 1:
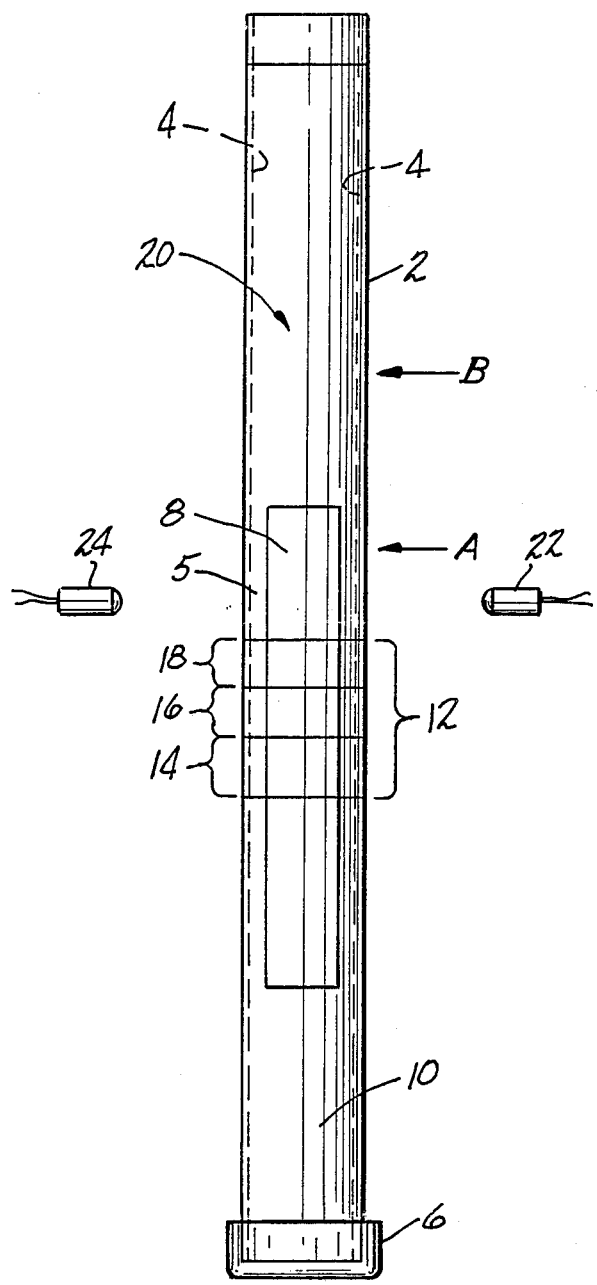

United States Patent [19]

Levine et al.

[11] Patent Number: 4,952,054

[45] Date of Patent: Aug. 28, 1990

[54] CORRECTION OF BLOOD COUNT TUBE READINGS

[76] Inventors: Robert A. Levine, 31 Pilgrim La., Guilford, Conn. 06437; Stephen C. Wardlaw, 191 N. Cove Rd., Old Saybrook, Conn. 06475

[21] Appl. No.: 303,120

[22] Filed: Jan. 30, 1989

[51] Int. Cl.⁵ .................. G01B 11/08; G01B 11/12; B01D 21/26

[52] U.S. Cl. .................. 356/39; 73/61.1 R; 128/771; 356/384

[58] Field of Search .......... 356/39, 382, 384; 73/1 J, 61.1 R; 128/771

[56] References Cited

U.S. PATENT DOCUMENTS 4,774,965  10/1988  Rodriguez et al. .......... 73/61.1 R X

*Primary Examiner*—Vincent P. McGraw
*Attorney, Agent, or Firm*—William W. Jones

[57] ABSTRACT

The method of correcting readings of cell counts in a centrifuged blood sample contained in a transparent tube which also contains a transparent cylindrical float. Light absorption measurements are made at different locations in the tube. A beam of light is directed through the tube and the float and a light absorption reading is taken. A light beam is also directed through the sample above the float and another absorption reading is taken. The ratio of the two readings is determined and compared to a target ratio that is precalculated from an ideal tube and float. Any deviations from the target ratio are proportional to correction factors which are applied to the cell readings taken. A colorant is added to the sample to impart the light absorption capability thereto.

5 Claims, 1 Drawing Sheet

CORRECTION OF BLOOD COUNT TUBE READINGS

This invention relates to the measurement of one or more constituent layers in a complex material mixture, and more particularly, to volumetric measurements in a centrifuged sample, with the application of correction factors to correct for dimensional variations in the paraphenalia used to contain the sample. When the method of this invention is used to measure blood cell counts the results are "true" blood cell counts, not "apparent" blood cell counts. U.S. Pat. No. 4,774,965 Rodriguez et al, granted Oct. 4, 1988 discloses another solution to the problem solved by the method of this invention.

A technique has been developed to measure constituent layers in a complex material mixture by centrifuging a sample of the material mixture in a transparent capillary, or other tube, which contains a float. The float is preferably cylindrical and formed from a transparent plastic material having a specific gravity which causes it to settle into the centrifuged mixture to a degree which creates a free volume annulus in the tube into which annulus the layer or layers to be measured will settle. The layers to be measured are thus physically elongated, and can be more easily and accurately measured. This technique has been used to measure blood cell counts, and is described in U.S. Pat. Nos. 4,027,660, issued June 7, 1977; 4,082,085, issued Apr. 4, 1978; 4,156,570 issued May 29, 1979; and others.

The accuracy of the aforesaid technique depends on the manufacturer's ability to hold the capillary tube ID's and the float OD's to very tight tolerances. The magnification factor for the elongated constituent layers, when the technique is used is preferred in its commercial form, is about 10. This means that any layer which is expanded by the technique will be 10 times longer using the float than it would be without using the float. In order to achieve this magnitude of elongation, the tube ID will be maintained at 0.06605 inch, and the float OD will be maintained at 0.06285 inch. Thus the annulus is preferably only 0.0016 of an inch thick, i.e. in the radial direction of the tube and float. It will be appreciated that minor variations in either the tube ID or the float OD, especially if additive, can result in changes in the annulus thickness which can cause inaccurate readings. For example, a tube which is slightly oversize, i.e. 0.00016 inch too large, plus a slightly undersized float, i.e. 0.00011 too small will result in a reduction of the observed band lengths in the annulus of 8%.

This invention relates to a method for detecting variations from the norm in the annulus thickness, and determining an appropriate correction factor which is applied to the actual measured band lengths to compensate for any annulus variations, whereby "true" readings can be derived. The method of this invention is based on the measurement of light absorbed in a colored medium in the tube, as a basis for determining the actual radial thickness of the annulus. The colored medium in the tube is preferably the plasma layer in a centrifuged sample of blood, which is colored by a stain, such as acridine orange. The stain is disposed in the tube for differentially coloring white blood cell and platelet layers in the centrifuged blood sample, in the prior art disclosed in the above-noted U.S. patents. Alternatively, a colored fluid, such as an oil, could be added to the blood sample. When the latter alternative is used, the colored fluid should be immiscible with the blood sample, and possess a specific gravity such that it will settle into the annulus during centrifugation, and also extend above the float and annulus. Thus the oil or the like should have a specific gravity between that of the platelets and the plasma. The immiscibility of the fluid will ensure that none of the materials in the blood sample being measured will interfere with the ability of the fluid to transmit light. Regarding both embodiments, two measurements of absorbed light are taken from the sample. One measurement is taken of absorbed light in the stained portion of the plasma layer (or the oil layer) disposed in the annulus, and the other measurement is taken in the stained plasma portion (or the oil layer portion) above the float, and thus above the annulus.

If the tube ID and the float OD are sized so as to form an annulus with a proper radial thickness, then the amount of light absorbed in the annulus reading will be a preset proportion of the amount of light absorbed in the reading taken across the full tube bore, i.e., above the float and the annulus. The instrument used to make the light absorption readings to a photometer incorporated into an instrument of the type shown in U.S. Pat. No. 4,558,947 or U.S. Pat. No. 4,683,579, for example. Photometers can detect differences in light absorption to one part per thousand accuracy. The reason that the aforesaid method is viable is that, regardless of the amount of acridine orange in a given blood sample, or the color intensity in the oil layer, the light absorption in both regions of the tube where readings are taken is directly proportional to the length that the light must travel along each path through the sample. Since the float is colorless, it does not absorb any of the light passing through the annulus and thus it does not adversely effect the readings.

It is therefore an object of this invention to provide a method for determining deviations in annulus thickness from the norm in a material layer volume measuring system.

It is a further object of this invention to provide a method of the character described which measures light absorption in a colored medium disposed in the annulus and compares the latter with light absorption in the colored medium outside of the annulus.

It is an additional object of this invention to provide a method of the character described which automatically corrects errors in volume measurements arising from detected deviations from the norm of the annulus thickness.

Figure 2:
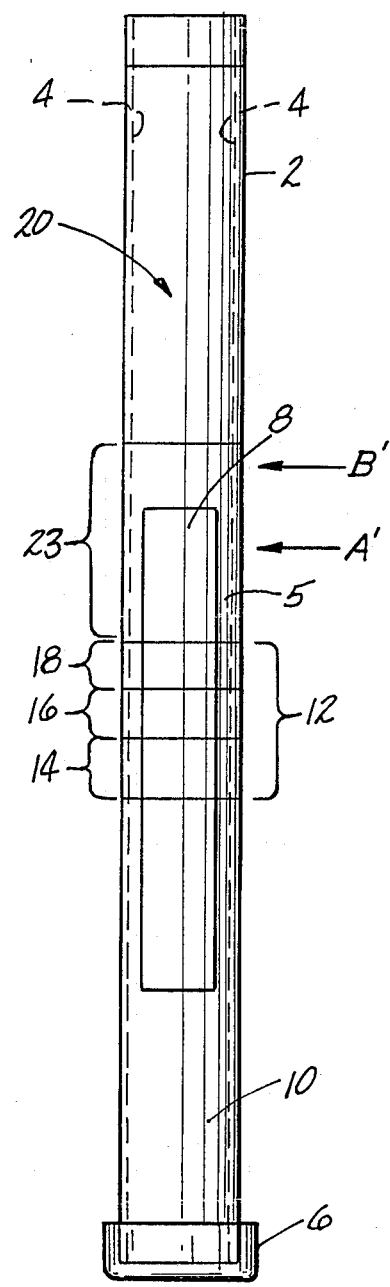

These and other objects and advantages of the invention will become more readily apparent from the following detailed description of two embodiments thereof, when taken in conjunction with the accompanying drawings, in which:

FIG. 1 is a side elevational view of a capillary tube and float combination used for performing blood cell counts in accordance with this invention; and FIG. 2 is a similar view of a second tube and float combination utilized in performing the method of this invention.

In the drawings, like numerals are used to identify equivalent structure in each figure. The tube 2 is a transparent capillary tube which has constant diameter bore 4. The bottom of the tube bore 4 is closed with a plastic cap 6, or the like during centrifugation of the sample in the tube 2. A generally cylindrical transparent plastic float 8 is disposed in the tube bore 4. The OD of the float 8 is a predetermined amount smaller than the diameter of the tube bore 4, so that a free space annulus 5 is formed in the tube. The specific gravity of the float 8 is such that it settles into the packed red blood cell layer 10 when the blood sample is centrifuged. The float 8 extends through the white cell layer (or buffey coat) 12 and into the plasma layer 20 of the centrifuged blood sample. The granulocyte, lymphocyte/monocyte, and platelet layers 14, 16 and 18 of the buffy coat 12 are disposed in the annulus 5, and are thus physically elongated to enable accurate cell counts to be obtained by measuring the axial length of all of the expanded cell bands 14, 16 and 18. A stain such as acridine orange is added to differentially color the cell bands 14, 16 and 18. The plasma layer 20 is also colored by the stain. After the sample is centrifuged, the plasma layer 20 will be clear and devoid of light-diffracting debris.

The instrument in which the readings are taken has a programmed onboard microprocessor which converts the axial measurements into cell counts. The accuracy of the cell counts of course depends on the tube bore 4 and the float 8 being formed with the proper dimensions so that the annulus 5 will be provided with the proper radial thickness. In the commercial form of the blood sampling tube and float, the tube bore is formed with a target radius of 841.5 ur, and the float radius is formed with a target radius of 798 ur. These dimensions will provide an annulus radial thickness which produces an expansion factor of about 10 of the cell bands in the annulus. This expansion factor is proportional to the ratio of the square of the tube bore radius to the difference between the squares of the tube bore radius and the float radius. Thus detected differences in this ratio which deviate from the norm or target ratio will indicate deviations in the annulus thickness from the norm or target annulus thickness. These deviations from the norm are depicted in the present invention by measuring light absorption values in the annulus and above the float. In the embodiment shown in FIG. 1, light transmission through the stained plasma layer 20 is measured along lines perpendicular to the axis of the tube 2: at point A, through the annulus 5 and the float; and at point B, through the plasma above the annulus. Light source 22 and photometer 24 (shown schematically) are used to obtain the absorption readings. The tube 2 will be shifted along its axis to make the two readings. The beam of light from the light source 22 must pass through the axis of the tube 2 and float 8 to obtain dependable data.

By way of example, if a tube were formed with an enlarged bore radius of 851.5 ur, the expansion factor of cell layers in the annulus 5 would be about 8. Thus about a 20% error in cell counts would result. Using this invention to detect the deviation, the ratio of the distance of the paths that a light beam must pass through the colored plasma in the annulus, and above the annulus are pre-inputted into the microprocessor. For the above-noted target tube bore and float which produces the 10 expansion factor, this inputted ratio is 19.3448/1. If a tube having the aforesaid enlarged bore radius of 851.5 ur the light path ratio would be 15.9159/1, a 21.5% difference from the target light path ratio. It will be noted that the source of the light path ratio deviations is irrelevant, so long as they are detected. If the ratio deviates downwardly, than the annulus is too thick, and if the ratio deviates upwardly, then the annulus is too thin. The microprocessor in the instrument will be programmed to make the necessary mathmatical corrections in cell counts when deviations from the norm are noted so that the corrected cell count data will be displayed.

In the embodiment shown in FIG. 2, a layer 23 of a clear colored oil, or other clear colored material which is immiscible with the blood sample, is disposed in the tube 2. The layer 20 has a specific gravity such that is sandwiched between the platelet layer 18 and the plasma 20. The layer 23 thus is partly disposed in the annulus 5, and also extends above the top of the float 8. The two readings are taken through the layer 23 in the annulus 5 and above the float 8 as previously described.

It will be readily appreciated that the invention can be used to detect deviations in annulus thickness in the blood sampling tubes of the prior art, whereby corrections in derived blood count data can be made. The light absorption readings can be taken in a modified blood count measuring instrument, or in a separate instrument specifically designed for that purpose. The results of the absorption readings are independent of the amount of colorant in the layer being measured for light absorption/transmission.

Since many changes and variations of the disclosed embodiment of the invention may be made without departing from the inventive concept, it is not intended to limit the invention otherwise than as required by the appended claims.

What is claimed is:

1. A method for detecting the magnitude of thickness deviations from a target radial thickness of an annulus formed between a transparent tube bore and a transparent solid cylindrical body disposed coaxially with and in said tube bore, and said tube bore also containing a clear colored fluid with a first portion thereof being disposed in said annulus, and a second portion thereof being located beyond one end of said cylindrical body, said method comprising the steps of:
   (a) determining the actual ratio of light absorbed from:
      (i) a first beam of light transmitted diametrically through the tube and body and through said first portion of said fluid; and
      (ii) a second beam of light transmitted diametrically through the tube and through said second portion of said fluid;
   (b) comparing said actual ratio with a predetermined ratio of light absorption of light beams transmitted along said first and second paths when the tube bore and body diameters are sized to create the target radial thickness in the annulus; and
   (c) calculating any amount of deviation between said actual ratio and said predetermined ratio thereby providing an indication of the magnitude of actual annulus deviations from said target thickness.

2. The method of claim 1 wherein said colored fluid is a stained plasma layer of a centrifuged sample of blood disposed in the tube.

3. The method of claim 1 wherein said colored fluid is a fluid which is substantially immiscible with other fluids in said tube bore.

4. A method of obtaining a correction factor for correcting apparent material layer volume values derived from a centrifuged fluid material sample which is contained in a transparent tube, wherein the material layers are disposed in an annulus in the tube between the bore wall of the tube and a transparent, material layer-elongating, solid cylindrical float in the tube, and wherein the tube contains a clear colored fluid band, which colored fluid is substantially immiscible with the fluid material sample in the tube, said method comprising the steps of:

(a) determining the actual ratio of light absorbed from:
  (i) a first beam of light transmitted along a first path diametrically through the tube and float and through a first portion of said colored fluid band disposed in said annulus; and
  (ii) a second beam of light transmitted along a second path diametrically through the tube and through a second portion of said colored fluid located beyond one end of the float;
(b) comparing said actual ratio with a predetermined ratio of light absorbtion found when the tube bore and float diameter are sized to create a target radial thickness in said annulus which will produce accurate material layer volume values; and
(c) using any variation found between the actual ratio and the predetermined ratio to calculate said correction factor.

5. A method of obtaining a correction factor for correcting apparent blood cell counts derived from a centrifuged stained sample of blood contained in a transparent capillary tube having a transparent cell layer-elongating solid cylindrical float in the tube, said method comprising the steps of:

(a) determining the actual ratio of light absorbed from:
  (i) a first beam of light transmitted along a first path diametrically through the tube and float, and through a portion of stained blood plasma disposed in a free annulus located between the tube and float; and
  (ii) a second beam of light transmitted along a second path diametrically through the tube and through a portion of the stained blood plasma located beyond one end of the float;
(b) comparing said actual ratio with a predetermined ratio of light absorption found when the tube bore and float diameter are sized to create a target radial thickness for said free space annulus which will produce accurate cell counts; and
(c) using any variation found between the actual ratio and the predetermined ratio to calculate said correction factor.

* * * * *